(12) United States Patent
Harning et al.

(10) Patent No.: US 9,700,580 B1
(45) Date of Patent: Jul. 11, 2017

(54) METHOD FOR CANCER TREATMENT

(71) Applicants: Marguerite Harning, Prescott, AZ (US); Robert Koppany, Prescott, AZ (US)

(72) Inventors: Marguerite Harning, Prescott, AZ (US); Robert Koppany, Prescott, AZ (US)

( * ) Notice: Subject to any disclaimer, the term of this patent is extended or adjusted under 35 U.S.C. 154(b) by 0 days.

(21) Appl. No.: 15/181,773

(22) Filed: Jun. 14, 2016

(51) Int. Cl.
*A61K 33/36* (2006.01)
*A61K 9/00* (2006.01)

(52) U.S. Cl.
CPC ............ *A61K 33/36* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 6,720,011 B1 | 4/2004 | Zhang | |
| 6,723,351 B2 | 4/2004 | Warrell, Jr. et al. | |
| 6,875,451 B2 | 4/2005 | Ellison et al. | |
| 6,884,439 B2 | 4/2005 | Warrell, Jr. et al. | |
| 2002/0013371 A1* | 1/2002 | Warrell, Jr. | A61K 31/285 514/623 |
| 2016/0015743 A1* | 1/2016 | Chen | C12Q 1/6886 424/623 |

OTHER PUBLICATIONS

Zhou et al., "Arsenic Trioxide for Non Acute Promyelocytic Leukemia Hematological Malignancies: A New Frontier", Journal of Blood Disorders 1(4), 2014, pp. 1-9.*
Cancerconnect.com. "Patients die unexpectedly following treatment with arsenic trioxide", Blood, vol. 98, No. 2, pp. 266-271, 2001.*
Liu et al., "Opposing effects of arsenic trioxide on hepatocellular carcinomas in mice", Cancer Sci, 2006, vol. 97, No. 7, pp. 675-681.*
Thermo Fisher Scientific ([retrieved from on-line website: https://www.thermofisher.com/order/catalog/product/10010031, last visit Nov. 23, 2016]).*
Gao et al., "Effects of arsenic trioxide under different administration ways on T-Cell lymphoma xenografts in nude mice", Chinese Journal of Cancer 28:2, 127-131, 2009.*
American Cancer Society, "When someone you know has cancer", 2015, pp. 1-3 ([retrieved from on-line website: http://www.cancer.org/treatment/understandingyourdiagnosis/talkingaboutcancer/whensomeoneyouknowhascancer/when-somebody-you-know-has-cancer-cancer-treatment-questions, last visit Nov. 27, 2016]).*
Jong et al., "Of Mice and Humans: Are They the Same?—Implications in Cancer Translational Research," Focus on molecular imaging, 2010, pp. 501-504.*

* cited by examiner

*Primary Examiner* — Ernst V Arnold
*Assistant Examiner* — Kyung Sook Chang
(74) *Attorney, Agent, or Firm* — Karish & Bjorgum, PC

(57) ABSTRACT

A method of treating humans with cancer by intravenously administering a single dose of arsenic trioxide in a phosphate buffered saline solution having a pH less than 8.0 in a dosage amount of between 6.0 and 7.0 mg/Kg according to the weight of the patient.

5 Claims, No Drawings

METHOD FOR CANCER TREATMENT

FIELD OF THE INVENTION

The present invention relates generally to methods for the treatment of cancer in humans and more specifically to the use of arsenic trioxide for such treatment.

BACKGROUND OF THE INVENTION

Cancer is characterized primarily by an increase in the number of abnormal cells derived from a given normal tissue, invasion of adjacent tissues by these abnormal cells, and spread of malignant cells to regional lymph nodes and to distant sites (metastasis). Clinical data and molecular biologic studies indicate that cancer is a multi-step process that begins with minor pre-neoplastic changes which may under certain conditions progress to neoplasia. Treatment for patients having cancer may include the utilization of drugs, chemotherapy, radiation and in some cases surgery. The particular treatment which is selected is dependent on a number of factors including the condition of the patient and the type of cancer that is to be treated.

Arsenic has been considered to be both poison and a drug for a long time in both Western and Chinese medical practices. In the latter part of the $19^{th}$ Century, arsenic was used frequently in attempts to treat diseases of the blood in the West. In 1878 it was reported that treatment of a leukemic patient with Fowler's (arsenic) solutions reduced markedly the count of white blood cells. Further interest in the use of Fowler's solution as a palliative agent to treat chronic myelogenous leukemia was reported. Fowler's solution was administered strictly as an oral composition. One of the long recognized effects of exposure to arsenic is skin cancer. The carcinogenicity of arsenic has since been demonstrated by the fact that it can induce chromosomal aberration gene amplification and cellular transformation. Because of the known carcinogenic effect of arsenic, it has not been widely used in humans in Western medicine.

Even with the known carcinogenic effect of arsenic and its toxicity, arsenic has been administered using arsenic trioxide formulations primarily for the treatment of leukemia. Such treatment typically has involved the administration of a plurality of doses of arsenic trioxide over a period of time. For example, U.S. Pat. No. 6,723,351 issued to Warrell, Jr. et al. provides a method of treating acute promyelogenous leukemia by administering 0.15 mg/kg arsenic trioxide once per day for a period of up to five weeks.

U.S. Pat. No. 6,875,451 to Ellison discloses administering arsenic trioxide to a cancer patient having solid tumors daily in amounts from about 10 micrograms to about 200 mgs, and also discloses that such treatment is done with at least one other therapeutic agent such as a chemotherapeutic agent or a radiotherapeutic agent and specifically discloses the administration of arsenic trioxide intravenously in a total daily dose of from 0.5 milligrams to 1.5 mgs. U.S. Pat. No. 6,720,011 to Zhang discloses a method of treating leukemia by administering an aqueous solution of 0.1% to 1% by weight of arsenic trioxide, 0.8% by weight sodium chloride, 10% by weight glucose and water on a daily basis for approximately two to four weeks.

From the above discussion, it is well known that arsenic is both a poison and a carcinogenic agent but that arsenic is still used in treating patients with leukemia and in some instances with solid tumors. It is also clear that there are many different types of cancers, each of which requires a unique treatment protocol that is modified according to the presence of factors predicting for a risk of treatment failure. Thus the development of a broad spectrum anti-cancer agent is extremely desirable.

SUMMARY OF THE INVENTION

Despite the conflicting reports in the prior art concerning the benefits and risks of the administration of arsenic to patients, applicants have discovered that arsenic trioxide when properly administered has broad applicability in the treatment of all types of cancer. The invention described herein encompasses a method of treatment of cancer in humans which comprises administering to a human in need of the treatment by intravenous injection of a single therapeutically effective dosage amount of between 6 and 7 mg/Kg of arsenic trioxide according to the weight of the human being treated.

DETAILED DESCRIPTION OF THE INVENTION

Applicants have recognized that every cancer cure which has been attempted for over 150 years has failed. As a result, applicants approached the subject of finding a cancer cure from the viewpoint of recognizing that cancers are really the supermen of cells in that they are supernormal cells and that the only way to kill such cancer cells is to poison them. Since cancer cells are more metabolically active than normal cells by definition, applicants decided to poison the cancer cells with something that would build up quickly to a toxic dose in the cancer cells, but not kill the normal cells. Applicants chose arsenic as the poison to be utilized to kill the cancer cells. The side effects on humans of arsenic are well known as are the problems with toxic doses. Arsenic has been investigated in multiple circumstances and applicants decided to use arsenic oxide as the poison of choice to kill the cancer cells because it causes less side effects than with other arsenic compounds such as arsenic triiodide, arsenic bromide, arsenic sulfides or calcium arsenide. Applicants also considered various ways of administration of the arsenic such as inhalation or oral administration, however, it has been shown that the inhalation of arsenic results in the arsenic becoming carcinogenic and worsens the patient's situation. It was also recognized that intramuscular injection of arsenic is much slower and less precise than intravenous administration and that oral administration has a decreased penetrance into the body compared to direct intravenous administration. It was recognized by applicants that if the arsenic compound is intravenously administered that a substantial amount of it is cleared from the body within one to two hours after the administration, that is, it has been recognized that 90% of the blood arsenic is cleared within one to two hours, the half times for the second and third clearance phase is from 30 to 200 hours.

Applicants also recognized that if arsenic is administered to a cancer patient on a sliding scale dosage over time as has been done in the prior art above referred to, that the cancer cells develop a resistance to the arsenic. As a result, applicants have developed a method where arsenic trioxide is delivered by intravenous injection as a single dose in an amount that is non-toxic but kills only the cancer cells.

Another problem recognized by applicants with cancer treatment is that when other medications are administered to the patient along with the arsenic trioxide, that such additional medications may very well stabilize the cell membrane of the cancer cells making it more impervious to the poison getting into the cancer cell. Such medications that can stabilize the cancer cells membranes are aspirin, Cisplatin, as well as other compounds and medications normally used to treat cancer patients. As a result, applicants' method is to utilize the intravenous injection without any other supportive chemotherapy or any other medication of any type besides appropriate anesthesia. By doing so, the cancer cell membrane stabilization is avoided. This results in the cancer cell membrane remaining porous so the arsenic trioxide can enter the cell and kill it.

In order to determine the effectiveness and toxicity of arsenic trioxide, applicants sponsored a study by a certified laboratory utilizing mice. The mice were divided into two different groups, a test group which would receive an appropriate dosage of arsenic trioxide and the other group would function as a control group and receive only a saline solution. Each of the mice were injected with a subcutaneous xenograft human lung tumor. Once the tumor size reached approximately 0.3 cubic centimeters, dosing solutions of arsenic trioxide were aspirated into a syringe and the syringe was inserted in the tail vein of each test group animal and dosing solutions in the amount of 6.5 mg/Kg according to the weight of the mice was administered over a two-hour period using an electronic syringe pump with the animal being anesthetized. After thirty days, the animals were euthanized and necropsies were performed and it was found that the tumors in the test group mice receiving the arsenic trioxide had a 65% reduction in tumor size as compared to the control group mice receiving no arsenic trioxide injection.

During the necropsies measurements and analyses were made on the tumor sizes, the hematology, the clinical chemistry, and the organ weights and the results thereof are set forth in the tables one through four below.

TABLE ONE

Tumor Measurement Summary
Study Number 150702-805

| Animal ID | Sex | Tumor Volume ($cm^3$) | | | | | | | | | |
|---|---|---|---|---|---|---|---|---|---|---|---|
| | | −25 | −18 | −11 | −4 | 1 | 4 | 11 | 18 | 26 | 30 |
| Group 1: Vehicle (Saline) | | | | | | | | | | | |
| G1F1 | F | 18.2 | 40.6 | 71.2 | 104.4 | 123.2 | 147.8 | 199.1 | 231.2 | 217.3 | 255.3 |
| G1F2 | F | 33.2 | 81.1 | 129.9 | 153.4 | 184.7 | 206.6 | 219.8 | 231.2 | 217.3 | 255.3 |
| G1F3 | F | 22.9 | 38.7 | 110.1 | 154.8 | 179.5 | 215.0 | 294.7 | 384.8 | 448.2 | 645.0 |
| G1F4 | F | 37.3 | 66.5 | 149.7 | 206.2 | 121.0 | 132.2 | 175.9 | 189.1 | 173.0 | 145.6 |
| G1F5 | F | 41.9 | 69.8 | 118.0 | 238.6 | 262.8 | 263.9 | 245.9 | 314.2 | 291.8 | 307.1 |
| G1F6 | F | 41.1 | 140.7 | 298.4 | 479.3 | 461.4 | 508.0 | 657.7 | 696.4 | 815.8 | 921.5 |
| Avg | | 32.43 | 72.88 | 146.22 | 222.78 | 222.08 | 245.91 | 298.85 | 341.17 | 360.53 | 421.63 |
| SD | | 9.82 | 37.24 | 78.95 | 134.00 | 128.20 | 137.06 | 180.51 | 187.67 | 243.26 | 298.16 |
| Group 2: Test Article (6.5 mg/kg) | | | | | | | | | | | |
| G2F1 | F | 9.4 | 59.7 | 109.2 | 129.0 | 148.4 | 144.3 | 109.4 | 67.9 | 77.6 | 147.5 |
| G2F2 | F | 27.9 | 43.5 | 96.3 | 132.9 | 121.0 | 93.1 | 94.9 | 80.1 | 69.6 | 113.9 |
| G2F3 | F | 23.4 | 53.8 | 112.2 | 165.5 | 55.0 | 55.0 | 32.7 | 16.3 | 7.9 | 7.3 |
| G2F4 | F | 14.6 | 82.8 | 162.1 | 181.4 | 233.9 | 213.6 | 258.5 | — | — | — |
| G2F5 | F | 38.7 | 115.3 | 168.6 | 248.9 | 176.6 | 142.7 | 108.2 | 99.3 | 69.3 | 27.2 |
| G2F6 | F | 35.5 | 63.3 | 185.7 | 452.0 | 374.4 | 388.8 | 348.2 | 513.7 | 616.9 | 992.2 |
| Avg | | 24.92 | 69.73 | 139.02 | 216.28 | 184.87 | 172.93 | 158.67 | 155.46 | 168.23 | 257.63 |
| SD | | 11.49 | 25.81 | 37.47 | 122.45 | 110.16 | 118.55 | 118.98 | 202.58 | 252.35 | 414.74 |

All of the control tumors gained weight. Four of the five mice on arsenic lost tumor volume. Two of these mice had dramatic loss in tumor volume, G2F3 and G2F5. Two mice lost volume and started regaining volume as the experiment progressed (G2F1 and G2F2). Aside from the test animal G2F6, the four mice remaining had an average loss of 40.9% in tumor volume, with the largest loss being 7.3 $cm^3$ from an initial volume of 55 $cm^3$, or 13.2% of the original volume (or a loss of 86.8% of the volume).

TABLE TWO

Hematology
Study Number 150702-805

| Group No. | Dose (mg/kg) | Animal ID | WBC ($10^3$/ul) | RBC ($10^4$/ul) | HGB (g/dl) | HCT % | PMN % | PMN Abs. x($10^3$/ul) | Lymph % | Lymph Abs. x($10^3$/ul) | Mono % | Mono Abs. x($10^3$/ul) |
|---|---|---|---|---|---|---|---|---|---|---|---|---|
| 1 | 0.0 | G1F1 | 2.30 | 7.92 | 12.6 | 36.6 | 26.6 | 0.61 | 67.0 | 1.54 | 4.3 | 0.10 |
| 1 | 0.0 | G1F2 | 1.70 | 8.87 | 13.9 | 39.1 | 44.3 | 0.75 | 46.5 | 0.82 | 3.6 | 0.06 |
| 1 | 0.0 | G1F3 | 2.80 | 7.28 | 11.1 | 32.9 | 31.0 | 0.87 | 60.0 | 1.68 | 1.0 | 0.03 |
| 1 | 0.0 | G1F4 | 3.20 | 7.62 | 11.5 | 33.0 | 18.9 | 0.60 | 72.1 | 2.31 | 5.6 | 0.18 |
| 1 | 0.0 | G1F5 | 3.80 | 6.23 | 12.7 | 37.1 | 21.1 | 0.80 | 72.8 | 2.77 | 3.4 | 0.13 |

TABLE TWO-continued

Hematology
Study Number 150702-805

| 1 | 0.0 | G1F6 | 6.50 | 7.30 | 11.3 | 34.1 | 14.1 | 0.92 | 70.0 | 4.55 | 6.6 | 0.43 |
|---|---|---|---|---|---|---|---|---|---|---|---|---|
|   |   | Ave | 3.38 | 7.87 | 12.2 | 35.5 | 26.0 | 0.76 | 65.1 | 2.28 | 4.1 | 0.15 |
|   |   | StDev | 1.69 | 0.61 | 1.1 | 2.5 | 10.7 | 0.13 | 9.4 | 1.30 | 1.9 | 0.14 |
| 2 | 6.5 | G2F1 | 5.70 | 8.27 | 12.5 | 35.7 | 19.8 | 1.13 | 61.3 | 3.49 | 7.6 | 0.43 |
| 2 | 6.5 | G2F2 | 3.90 | 8.01 | 11.9 | 34.9 | 18.5 | 0.72 | 73.0 | 2.85 | 8.2 | 0.24 |
| 2 | 6.5 | G2F3 | 5.10 | 8.24 | 12.7 | 37.3 | 25.0 | 1.28 | 50.0 | 2.55 | 2.0 | 0.10 |
| 2 | 6.5 | G2F4 | 1.90 | 5.01 | 8.7 | 24.3 | 28.0 | 0.53 | 84.0 | 1.22 | 6.0 | 0.15 |
| 2 | 6.5 | G2F5 | 5.40 | 7.73 | 11.5 | 33.7 | 65.3 | 2.99 | 27.7 | 1.50 | 12.8 | 0.69 |
| 2 | 6.5 | G2F6 | 2.30 | 8.13 | 13.0 | 38.5 | 38.3 | 0.88 | 53.6 | 1.23 | 4.3 | 0.10 |
|   |   | Ave | 4.06 | 7.57 | 11.7 | 34.1 | 30.8 | 1.25 | 54.9 | 2.14 | 6.8 | 0.29 |
|   |   | StDev | 1.63 | 1.27 | 1.6 | 5.1 | 13.9 | 0.89 | 15.6 | 0.96 | 3.7 | 0.23 |
| Reference Values |  | Ave | 4.86 | 8.60 | 13.7 | 45.6 | 30.8 | 1.49 | 61.9 | 2.95 | 4.3 | 0.26 |
| (CRL female 8-10 |  | Low | 1.42 | 6.82 | 10.9 | 34.9 | 14.0 | 0.43 | 23.6 | 0.49 | 0.9 | 0.03 |
| week) |  | High | 10.25 | 10.53 | 15.9 | 56.1 | 54.7 | 3.16 | 79.3 | 8.87 | 11.4 | 0.65 |

| Group No. | Dose (mg/kg) | Animal ID | Baso % | Baso Abs. x($10^3$/ul) | Platelet Count ($10^3$/ul) | MCV (fl) | MCH (pg) | MCHC (g/dl) | Reticulocyte % | Reticulocyte Abs. x($10^9$/L) |
|---|---|---|---|---|---|---|---|---|---|---|
| 1 | 0.0 | G1F1 | 0.4 | 0.01 | 973 | 46.0 | 15.9 | 34.4 | 222.00 | 2.8 |
| 1 | 0.0 | G1F2 | 0.6 | 0.01 | 962 | 44.0 | 15.7 | 35.5 | 381.00 | 4.3 |
| 1 | 0.0 | G1F3 | 0.0 | 0.00 | 1565 | 45.0 | 15.2 | 33.7 | 153.00 | 2.1 |
| 1 | 0.0 | G1F4 | 0.6 | 0.02 | 1052 | 43.0 | 15.1 | 34.8 | 221.00 | 2.9 |
| 1 | 0.0 | G1F5 | 0.3 | 0.01 | 936 | 45.0 | 15.4 | 34.2 | 346.00 | 4.2 |
| 1 | 0.0 | G1F6 | 0.2 | 0.01 | 1310 | 47.0 | 15.5 | 33.1 | 248.00 | 3.4 |
|   |   | Ave | 0.4 | 0.01 | 1133 | 45.0 | 15.5 | 34.3 | 261.63 | 3.3 |
|   |   | StDev | 0.2 | 0.01 | 252 | 1.4 | 0.3 | 0.8 | 85.53 | 0.9 |
| 2 | 6.5 | G2F1 | 0.4 | 0.02 | 989 | 43.0 | 16.1 | 35.0 | 331.00 | 4.0 |
| 2 | 6.5 | G2F2 | 0.5 | 0.02 | 1419 | 44.0 | 14.9 | 34.1 | 240.00 | 3.0 |
| 2 | 6.5 | G2F3 | 0.0 | 0.00 | 822 | 45.0 | 15.4 | 34.0 | 297.00 | 3.6 |
| 2 | 6.5 | G2F4 | 0.0 | 0.00 | 124 | 49.0 | 17.4 | 35.8 | 431.00 | 8.6 |
| 2 | 6.5 | G2F5 | 0.9 | 0.05 | 1201 | 44.0 | 14.9 | 34.1 | 340.00 | 4.4 |
| 2 | 6.5 | G2F6 | 0.4 | 0.01 | 989 | 47.0 | 16.0 | 33.6 | 333.00 | 4.1 |
|   |   | Ave | 0.4 | 0.02 | 924 | 45.3 | 15.6 | 34.5 | 328.67 | 4.6 |
|   |   | StDev | 0.3 | 0.02 | 443 | 2.3 | 1.0 | 0.8 | 62.43 | 2.0 |
| Reference Values |  | Ave | 0.6 | 0.03 | 1079 | 53.1 | 16.0 | 30.3 | NA | NA |
| (CRL female 8-10 |  | Low | 0.0 | 0.00 | 378 | 46.6 | 12.7 | 25.1 | — | — |
| week) |  | High | 2.2 | 0.21 | 1796 | 67.9 | 18.0 | 34.5 | — | — |

The red blood cell (RBC), hemoglobin, and hematocrit values decreased in the test animals. The white blood cells (WBC) were 1.22 times higher in the test subjects, while the polymorphonuclear cells (PMN) increased by 1.18 times. Monocytes in the test animals increased to 1.65 times the controls, while lymphocytes decreased to 0.84 that of the controls.

TABLE THREE

Clinical Chemistry
Study Number 150702-805

| Group No. | Dose (mg/kg) | Animal ID | ALK (U/L) | ALT (U/L) | AST (U/L) | ALB (g/dL) | TP (g/dL) | A/G ratio | GLOB (g/dL) | BILI-T (mg/dL) | BUN (mg/dL) |
|---|---|---|---|---|---|---|---|---|---|---|---|
| 1 | 0.0 | G1F1 | 74 | 22 | 44 | 2.7 | 4.4 | 1.6 | 1.7 | 0.1 | 18 |
| 1 | 0.0 | G1F2 | 75 | 32 | 85 | 2.6 | 4.6 | 1.3 | 2.0 | 0.1 | 26 |
| 1 | 0.0 | G1F3 | 61 | 67 | 155 | 2.3 | 4.2 | 1.2 | 1.9 | 0.1 | 23 |
| 1 | 0.0 | G1F4 | 78 | 38 | 233 | 2.5 | 4.7 | 1.1 | 2.2 | 0.1 | 22 |
| 1 | 0.0 | G1F5 | 87 | 249 | 505 | 2.6 | 4.1 | 1.6 | 1.6 | 0.1 | 24 |
| 1 | 0.0 | G1F6 | 58 | 23 | 57 | 2.3 | 4.0 | 1.4 | 1.7 | 0.1 | 25 |
|   |   | Ave | 72 | 72 | 180 | 2.5 | 4.3 | 1.4 | 1.9 | 0.1 | 23 |
|   |   | StDev | 11 | 88 | 174 | 0.2 | 0.3 | 0.2 | 0.2 | 0.0 | 3 |
| 2 | 6.5 | G2F1 | 76 | 47 | 124 | 2.6 | 4.3 | 1.4 | 1.6 | 0.1 | 19 |
| 2 | 6.5 | G2F2 | 61 | 145 | 73 | 2.8 | 4.8 | 1.2 | 2.2 | 0.1 | 16 |
| 2 | 6.5 | G2F3 | 73 | 297 | 382 | 2.5 | 4.4 | 1.3 | 1.9 | 0.1 | 25 |
| 2 | 6.5 | G2F4 | 34 | 18 | 67 | <3.0 | 4.3 | 0.8 | <0.3 | <0.3 | 21 |
| 2 | 6.5 | G2F5 | 37 | 21 | 71 | 2.2 | 4.2 | 1.1 | 2.0 | 0.1 | 21 |
| 2 | 6.5 | G2F6 | 90 | 46 | 113 | 2.4 | 4.2 | 1.3 | 1.8 | 0.1 | 17 |
|   |   | Ave | 62 | 96 | 136 | 2.4 | 4.4 | 1.2 | 1.9 | 0.1 | 20 |
|   |   | StDev | 22 | 109 | 122 | 0.2 | 0.2 | 0.2 | 0.2 | 0.0 | 3 |
| Reference Values |  | Ave | 164 | 64 | 132 | 3.4 | 5.7 | NA | NA | 0.3 | 19 |
| (CRL female 8-10 |  | Low | 76 | 31 | 47 | 2.8 | 4.8 | — | — | 0.2 | 11 |
| week) |  | High | 301 | 115 | 560 | 4.0 | 6.6 | — | — | 0.6 | 39 |

The alkaline phosphatase (ALK), alanine aminotransferase (ALT), and aspartate aminotransferase (AST) values decreased in the test animals to 0.75 that of the controls. The arsenic animal's albumin decreased to 0.96 that of the controls while the blood urea nitrogen (BUN) decreased to 0.86 that of the controls. Total protein, globin and bilirubin was unchanged between controls and the arsenic test subjects.

It should be noted on the post-experiment pathology reports that there is less than a 0.05 significant difference in the brain, heart, left kidney, or right kidney weights between the controls and arsenic given mice. The spleen values were larger by 1.097 in the arsenic animals compared to the controls. Perhaps, most significantly, the liver was 0.882 that of the arsenic mice compared to that of the controls. However, for the liver analysis only, if we disregard mouse G2F4

TABLE THREE

Clinical Chemistry (cont)
Study Number 150702-805

| Group No. | Dose (mg/kg) | Animal ID | CREAT (mg/dL) | CHOL (mg/dL) | GLUC (mg/dL) | $Ca^{2+}$ (mg/dL) | Phos (mg/dL) | $Cl^+$ (meq/L) | $K^+$ (meq/L) | $Na^+$ (meq/L) | Hemolysis Index |
|---|---|---|---|---|---|---|---|---|---|---|---|
| 1 | 0.0 | G1F1 | 0.2 | 106 | 155 | 9.0 | 8.2 | 112 | 3.4 | 150 | N |
| 1 | 0.0 | G1F2 | 0.3 | 122 | 126 | 9.3 | 11.5 | 108 | 4.6 | 149 | N |
| 1 | 0.0 | G1F3 | 0.2 | 115 | 148 | 9.0 | 12.0 | 113 | 4.5 | 153 | N |
| 1 | 0.0 | G1F4 | 0.3 | 111 | 155 | 8.6 | 10.0 | 112 | 4.6 | 151 | N |
| 1 | 0.0 | G1F5 | 0.2 | 80 | 142 | 9.6 | 11.8 | 111 | 5.2 | 149 | H |
| 1 | 0.0 | G1F6 | 0.2 | 73 | 127 | 9.0 | 12.2 | 113 | 4.5 | 151 | N |
| | | Ave | 0.2 | 101 | 142 | 9.1 | 11.0 | 112 | 4.5 | 151 | — |
| | | StDev | 0.1 | 20 | 13 | 0.3 | 1.6 | 2 | 0.6 | 2 | — |
| 2 | 6.5 | G2F1 | 0.2 | 98 | 197 | 9.3 | 7.6 | 111 | 4.5 | 148 | N |
| 2 | 6.5 | G2F2 | 0.2 | 94 | 119 | 9.2 | 8.4 | 112 | 4.3 | 151 | N |
| 2 | 6.5 | G2F3 | 0.2 | 102 | 181 | 8.7 | 9.8 | 111 | 4.9 | 146 | H |
| 2 | 6.5 | G2F4 | <0.3 | 53 | 121 | 9.1 | 9.0 | — | — | — | N |
| 2 | 6.5 | G2F5 | 0.2 | 58 | 118 | 9.3 | 9.0 | 116 | 4.0 | 157 | N |
| 2 | 6.5 | G2F6 | 0.2 | 107 | 169 | 8.9 | 8.2 | 112 | 3.8 | 149 | N |
| | | Ave | 0.2 | 85 | 154 | 9.1 | 6.7 | 112 | 4.3 | 151 | — |
| | | StDev | 0.0 | 24 | 39 | 0.2 | 0.8 | 2 | 0.4 | 4 | — |
| Reference Values | | Ave | 0.3 | 133 | 191 | 10.8 | 11.5 | 116 | 8.6 | 151 | N |
| (CRL female 8-10 | | Low | 0.2 | 98 | 149 | 9.6 | 6.1 | 109 | 7.0 | 141 | — |
| week) | | High | 0.4 | 202 | 271 | 12.1 | 17.3 | 133 | 10.8 | 165 | — |

The test animal's cholesterol decreased to 0.84 that of the controls, while the glucose increased to 1.08 times that of the control. The calcium, creatinine, chloride, and sodium were unchanged from the controls. The phosphate in the arsenic test animals decreased slightly to 0.99 that of the controls while the potassium decreased slightly to 0.955 that of the controls.

who died and mouse G2F6 who was unaffected by the arsenic, the liver average of the test animals is 0.9351 that of the controls, which is quite reasonable. It should be noted that none of the arsenic mice organ values are drastically different from the controls except for that of the tumor weights, which is 0.494 that of the controls in the mice receiving the arsenic. Again, if we eliminate G2F4 and

TABLE FOUR

Organ Weights
Study Number 150702-805

| Animal ID | Sec | Brain (g) | Heart (g) | Spleen (g) | Right Kidney (g) | Left Kidney (g) | Liver w/ Gallbladder (g) | Tumor (g) |
|---|---|---|---|---|---|---|---|---|
| Group 1: Vehicle (Saline) | | | | | | | | |
| G1F1 | F | 0.4425 | 0.1608 | 0.1404 | 0.1919 | 0.2218 | 1.4240 | 0.2056 |
| G1F2 | F | 0.4273 | 0.1795 | 0.1335 | 0.2351 | 0.2225 | 1.7489 | 0.1994 |
| G1F3 | F | 0.4626 | 0.1683 | 0.0892 | 0.2370 | 0.2180 | 1.5123 | 0.4947 |
| G1F4 | F | 0.4365 | 0.1605 | 0.1419 | 0.2101 | 0.2232 | 1.4974 | 0.1491 |
| G1F5 | F | 0.4390 | 0.1733 | 0.1661 | 0.2367 | 0.2296 | 1.4944 | 0.2223 |
| G1F6 | F | 0.4545 | 0.2000 | 0.1565 | 0.2104 | 0.2275 | 1.7940 | 0.7604 |
| Mean | | 0.4421 | 0.1737 | 0.1379 | 0.2202 | 0.2238 | 1.5782 | 0.3386 |
| S.D. | | 0.0102 | 0.0148 | 0.0267 | 0.0188 | 0.0042 | 0.1528 | 0.2403 |
| Group 2: Test Article (6.5 mg/kg) | | | | | | | | |
| G2F1 | F | 0.4587 | 0.1730 | 0.1467 | 0.2292 | 0.2579 | 1.5739 | 0.0780 |
| G2F2 | F | 0.4426 | 0.1866 | 0.1454 | 0.2173 | 0.2152 | 1.6061 | 0.0979 |
| G2F3 | F | 0.4069 | 0.1989 | 0.1335 | 0.1675 | 0.1838 | 1.2410 | 0.0106 |
| G2F4 | F | 0.4358 | 0.1762 | 0.1377 | 0.1819 | 0.1679 | 1.1603 | 0.2326 |
| G2F5 | F | 0.4310 | 0.1378 | 0.2369 | 0.2057 | 0.2428 | 1.5821 | 0.0301 |
| G2F6 | F | 0.4027 | 0.1706 | 0.1073 | 0.1946 | 0.2138 | 1.3585 | 0.5586 |
| Mean | | 0.4296 | 0.1739 | 0.1513 | 0.1994 | 0.2136 | 1.4020 | 0.1678 |
| S.D. | | 0.0214 | 0.0205 | 0.0443 | 0.0228 | 0.0340 | 0.1811 | 0.2059 |

G2F6, we have an average of 0.05415 or 0.1599 of the controls, an 84% reduction of the tumors. These are good numbers.

Applicants believe that only cancer patients who have tried every other possible treatment for cancer with no results or with the cancer returning after remission should utilize the cancer treatment of the present invention. Such individuals should be hospitalized for three days to allow the arsenic trioxide to flush out of their systems and then monitored in-hospital an additional four days to assure the patients do not take any membrane stabilizers. The arsenic trioxide should be intravenously administered, typically by a syringe infusion over a two-hour period and as above indicated, no other treatment or medication of any type should be administered to the patient besides anesthesia. The preferred dosage is 6.5 mg/Kg depending upon the weight of the individual receiving the treatment. It is also recognized that there may be a plus or minus 0.5 mg/Kg of variation from the desired and preferable dosage.

The solution for the single dose arsenic trioxide intravenous injection was prepared by solubilizing solid high purity arsenic trioxide in an aqueous solution of high pH such as pH greater than 12. For example, a solution of sodium hydroxide may be used. However, this solution is too basic to be used as a pharmaceutical composition. This solution was then diluted using a phosphate buffered saline solution to a final concentration having a pH less than 8.0.

What is claimed is:

1. A method of treatment of cancer in humans comprising: administering to a human admitted to a hospital and in need of said treatment by intravenous injection of a single therapeutically effective dosage amount of between 6.0 and 7.0 mg/Kg of arsenic trioxide according to the weight of the human being treated, in the absence of any other treatment or medication that can stabilize the cancer cell membrane, anesthetizing the human during the administration of the arsenic trioxide, and retaining the human in the hospital for at least three days after the administration of the arsenic trioxide.

2. The method of claim 1 wherein said arsenic trioxide is administered over a two-hour period.

3. The method of claim 1 wherein said arsenic trioxide is contained in a phosphate buffered saline solution having a pH less than 8.0.

4. The method of claim 1 wherein said dosage of arsenic trioxide is administered intravenously by using an electronic syringe pump.

5. The method of claim 1 wherein said dosage amount is 6.5 mg/Kg of arsenic trioxide.

\* \* \* \* \*